(12) United States Patent
Moore

(10) Patent No.: US 8,403,898 B2
(45) Date of Patent: Mar. 26, 2013

(54) APPARATUS AND METHOD FOR DEPLOYING A SURGICAL PREPARATION

(76) Inventor: Mark R. Moore, Westlake, LA (US)

( * ) Notice: Subject to any disclaimer, the term of this patent is extended or adjusted under 35 U.S.C. 154(b) by 855 days.

(21) Appl. No.: 11/602,542

(22) Filed: Nov. 21, 2006

(65) Prior Publication Data

US 2008/0119801 A1   May 22, 2008

(51) Int. Cl.
*A61M 35/00* (2006.01)
(52) U.S. Cl. .......... 604/293; 604/290; 604/292
(58) Field of Classification Search .......... 604/289–293, 604/408; 602/3, 79; 606/202
See application file for complete search history.

(56) References Cited

U.S. PATENT DOCUMENTS

| | | |
|---|---|---|
| 871,689 A | 11/1907 | Ganzhom |
| 2,690,747 A | 10/1954 | Frallic |
| 3,327,705 A * | 6/1967 | Spira et al. .......... 602/48 |
| 4,808,172 A | 2/1989 | Murata |
| 4,858,604 A | 8/1989 | Konishi |
| 5,312,385 A * | 5/1994 | Greco .......... 604/356 |
| 5,592,953 A * | 1/1997 | Delao .......... 128/882 |
| 5,702,356 A | 12/1997 | Hathman |
| 5,769,806 A | 6/1998 | Radow |
| 5,823,977 A | 10/1998 | Dalyea |
| 6,007,564 A | 12/1999 | Haverstock |
| 6,241,697 B1 | 6/2001 | Augustine |
| 6,450,982 B1 * | 9/2002 | Peterson .......... 602/3 |
| 6,635,035 B1 * | 10/2003 | Marasco et al. .......... 604/290 |
| 6,664,434 B2 | 12/2003 | Cominsky |
| 6,992,233 B2 | 1/2006 | Drake et al. |
| 2004/0171998 A1 * | 9/2004 | Marasco, Jr. .......... 604/290 |

* cited by examiner

*Primary Examiner* — Lynne Anderson
(74) *Attorney, Agent, or Firm* — Schultz & Associates, P.C.

(57) ABSTRACT

A device used for applying an antiseptic preparation to a surgical site of a patient prior to surgery outside of an operating theater. A loose-fitting bag is provided which encloses the surgical site by securing the open end(s) to the patient by closing means. A method and apparatus are also provided for releasing antiseptic into the interior of the bag. The method provides that the surgical site can be scrubbed within the bag so as to properly prepare the skin for surgery. A temperature indicator for the antiseptic preparation is also provided.

26 Claims, 5 Drawing Sheets

APPARATUS AND METHOD FOR DEPLOYING A SURGICAL PREPARATION

FIELD OF THE INVENTION

This present invention relates to a method to an apparatus and method for applying antiseptic prior to surgery.

BACKGROUND

Surgical site infections are frequently caused by bacteria commonly found on the surface of the skin. Since 1867, when Joseph Lister discovered the link between microbes and patient mortality after operations, he coined the term "antiseptic" after discovering that certain surgical preparations could be applied before surgery to eliminate bacteria. Practitioners have used aseptic techniques to reduce post-operative infections ever since.

In order to reduce bacteria, antiseptics are used prior to conducting the surgery to clean and disinfect the surgical site. Types of antiseptics include alcohols, iodine or iodine-containing compounds and chlorohexidine gluconate among others. There are two primary types of iodine-containing compounds, tincture of iodine, and iodophors. Tincture of iodine is an alcohol solution and was one of the first antiseptics used. However, iodophors are more commonly used today to prepare a surgical site for surgery.

The most common aseptic technique for sterilizing a surgical site requires application of an antiseptic solution immediately prior to the surgical procedure in the sterile operating theater after the patient has been anesthetized. When performing surgery to the extremities, i.e. leg or arm, the entire extremity is typically cleaned with the antiseptic solution. A sponge is immersed in the antiseptic solution, then applied to an area of the extremity with a scrubbing action and then discarded. A new sponge is immersed into the antiseptic solution and applied to a different area of the extremity. This process is then repeated until the entire area has been scrubbed. The scrubbing action physically dislodges bacterial colonies. Once the scrubbing is completed, another antiseptic solution is reapplied with a sponge in a painting action using a new sponge with each repeated application. After this procedure the surgical personnel must wait at least five to seen minutes before beginning the surgical procedure. The delay is required to allow the antiseptic solution to disinfect the surgical site.

There are several problems with the prior art procedure for disinfecting a surgical site. During the application of the antiseptic solution to the extremity, numerous sponges are required to be used and discarded, thus creating waste that must be handled and properly discarded. There is also a possibility that the surgical site will not be completely covered, thus creating a potential for bacteria and other contaminants remaining during surgery and serving as a potential source for post-surgical infection. The application of the antiseptic solution is prone to splashing and uncontrolled spills. Excess antiseptic solution spills creating a potential safety hazard and a potential for infection.

The prior art procedure for applying the antiseptic solution is also costly and time consuming. Operating theaters are expensive to maintain and operate. The time that the antiseptic solution takes to be effective costs the patient and the hospital a significant amount of money. The delay also slows the throughput of the operating theater, thereby raising the cost of the procedure to the hospital and the operating staff.

The prior art procedure puts the patient at an increased risk of morbidity and mortality by increasing the amount of time the patient is under anesthesia.

The current invention provides a device and method for applying an antiseptic solution to a surgical site prior to surgery but outside the operating theater thus reducing anesthesia time along with operating room time and cost. The invention also contains the spills and reduces waste. Since the application of the antiseptic can be accomplished outside the operating theater, additional time and care can be used in applying the antiseptic, thereby reducing post-surgical infection.

Various prior art devices and methods have been used in the past to cover a wound, protect a wound site, or apply medicine to a wound site. But none of the prior art has been used to streamline application of a surgical antiseptic prior to surgery.

One example is U.S. Pat. No. 2,661,739 issued to Caskey. Caskey discloses a casing which is made from elastic material to fit against an extremity to hold an absorbent material against a wound. The casing is surrounded by a fabric jacket to hold the casing and absorbent material in place and exclude contamination from the environment. However, the casing is only disclosed to be used after a wound has occurred and it does not disclose using the device to pre-treat an area prior to surgery. Additionally, it does not allow for the scrubbing of medicine against the skin through the device.

Another example is U.S. Pat. No. 6,992,233 B2 issued to Drake, et al. Drake discloses a delivery system for a flowable medicine to a wound in a confined area. Flowable medicine is contained in a strip which is adhesively applied to the skin such that the medicine is delivered to the wound. The flowable medicine is released when removable seal is removed. Drake does not disclose using the device for application of medicine prior to a wound occurring or to a large area of the body. It is limited to the area covered by the strip. Drake also does not disclose scrubbing the medicine against the skin through the device.

A third example is U.S. Pat. No. 6,664,434 B2 issued to Cominsky. Cominsky discloses using a sealed bag around a wound to contain bodily fluids. The device includes an absorbent layer to absorb the bodily fluids exuding from a wound. It does not disclose using the bag prior to the wound or introduction of an antiseptic fluid within the bag. It also does not disclose the scrubbing of an antiseptic through the device.

SUMMARY OF THE INVENTION

A surgical preparation solution applicator is described for preparing a patient's skin for surgery prior to entering the surgical theater. More specifically, a device and method for facilitating application of antiseptic solution to a surgical site in a non-sterile environment is described.

The applicator, in one embodiment, includes a bag which is sealed on three sides and open on a fourth side. A resilient seal gasket is affixed to the open end of the applicator bag. The gasket fits snuggly around the patient's body forming a seal between the interior of the bag and patient's body. An antiseptic solution is then introduced into the application bag through either a port in the application bag, a solution deployment pouch within the application bag or through an opening between the gasket and the patients body. The gasket prevents the release of the antiseptic until removed.

The solution deployment pouch releases antiseptic into the bag once the gasket is secured. The pouch can take the form of a capsule in ducted communication with the application bag which is filled with the antiseptic solution. Other embodiments include one or more ports and/or one or more solution deployment pouches.

In another embodiment, the applicator bag employs other closing means to seal the open end of the application bag securely against the patient's body. This closing means can include but is not limited to a pressure inflatable cuff, a tourniquet, or a pressure strap fixed with a buckle or Velcro® closure.

In another embodiment, the application bag is open on two ends having a resilient seal gasket fixed at each end. In this embodiment, the patient's body is inserted through the seal gaskets at both open ends of the application bag.

In another embodiment, the application bag is suited well for use on a relatively flat area of the body, such as the back or abdomen. In this embodiment, the open end of the bag is secured to the patient with a disk-like adhesive strip. The adhesive strip temporarily adheres to the patient's body during the procedure and acts as a seal between the patient's body and the interior of the bag. After the adhesive is adhered to the patient's body, the antiseptic solution is released inside the application bag, either through a port or by a solution deployment pouch located inside the application bag.

At all places other than the seal gasket, the application bag is loose-fitting around the patient's body to allow the user to manipulate the bag freely and completely apply antiseptic around the body part being treated without breaking the seal of the gasket.

In the preferred embodiment, the application bag is used to disinfect the surgical site before the patient has undergone use of anesthesia. Because the patient is awake, the temperature of the antiseptic solution may be uncomfortable to the patient and increase surgery anxiety in the patient. For this reason, the invention further provides an inexpensive mechanism to monitor the temperature of the antiseptic solution prior to application to the patient. Matching the temperature of the antiseptic solution to the patient aids in reducing pre-surgery anxiety of the patient and therefore a more efficient application of the antiseptic solution.

In yet another preferred embodiment, sterile sponges or other devices used to apply the antiseptic solution to the body can be contained in sealed pouches secured to the inside of the application bag or inside the antiseptic pouch. When the antiseptic is deployed within the bag, the sterile sponges are used to apply the bag and then discarded with the bag prior to surgery.

After this process has been completed, the application bag contains the antiseptic and prevents outside bacteria and contaminants from contacting the treated area. The application bag is designed to remain in place until the patient is positioned in the operating theater. The application bag is removed immediately prior to surgery.

BRIEF DESCRIPTION OF THE DRAWINGS

In the detailed description of the preferred embodiments presented below, reference is made to the accompanying drawings.

DETAILED DESCRIPTION OF THE PREFERRED EMBODIMENTS

Figure 1A:
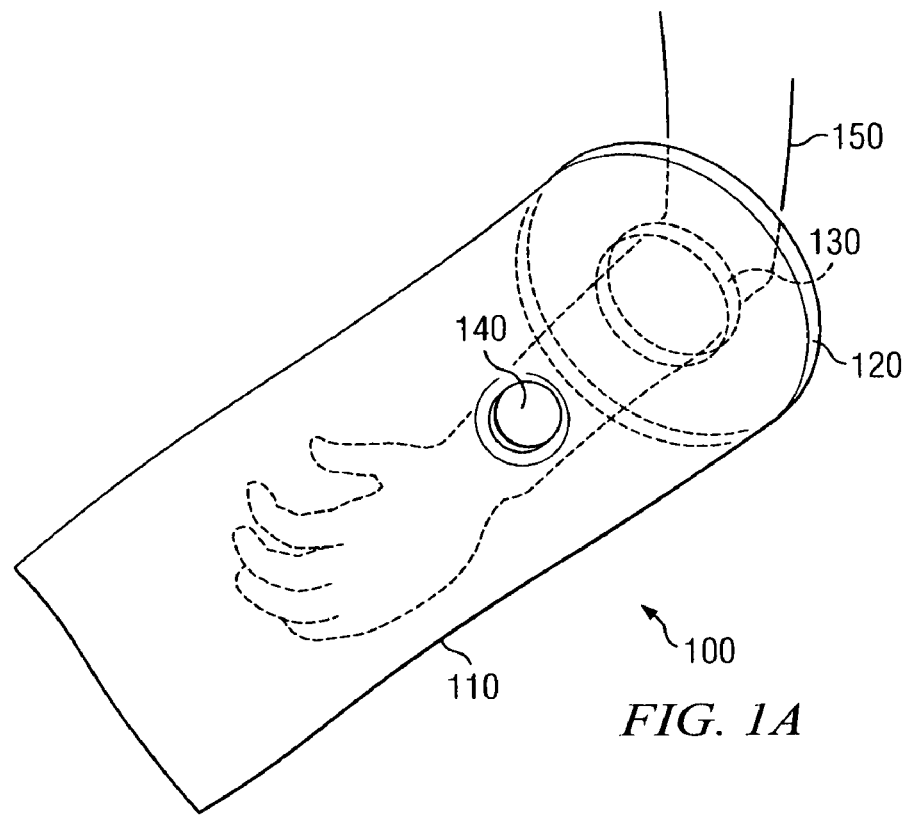
FIG. 1a is a perspective view of an embodiment of the invention showing the use of a flat neoprene gasket seal.
Figure 1B:
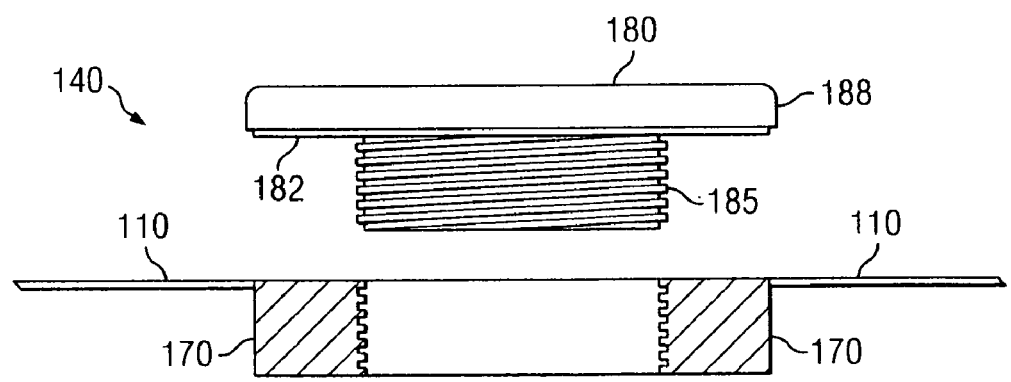
FIG. 1b is a cross sectional view of a preferred embodiment of fill/drain port.

FIG. 1a shows a preferred embodiment of solution applicator 100. Solution applicator 100 includes application bag 110. In the preferred embodiment, application bag 110 is made of HDPE (high density polyethylene) which is typically translucent, but not fully transparent. In other embodiments, the application bag can be made out of LDPE (low density polyethylene) and can be quite clear, but still not totally transparent. In other embodiments, LLDP (linear low density polyethylene) can be employed where a higher structural rigidity is required by the cleaning process. Other flexible sheeting can be used so long as it is inert with respect to the antiseptic solution.

In another preferred embodiment, the interior and/or exterior of the application bag can be textured to increase the effectiveness of the application of the antiseptic to the patient. If on the exterior of the application bag, the purpose of the texturing is to increase friction between the hands of the user and the exterior of the application bag to aid in manipulation of the application bag during use. If on the interior of the application bag, the textured surface is useful in scrubbing the surgical site to remove bacterial colonies. Examples of textures can include raised ribs, chevron patterns, diamond patterns or random "crinkling". Other plastics can be used if complete transparency is required for various cleaning processes. In other embodiments, the application bag can be color coded to indicate different sizes, different antiseptics contained within the bag or the proper operating theater for the patient.

In a preferred embodiment, application bag 110 can be formed from two identical or nearly-identical sized sheets. Both sheets will have the same or nearly the same shape. In a preferred embodiment, the two sheets are rectangular. All of the sides but one are sealed or fused by an adhesive or heat welding as known in the art, leaving the remaining side open. The flat format of the completed application bag increases the ease of storage and/or deployment of the bag from a roll or cardboard box as known in the art. The shape also promotes economy of manufacture.

In another preferred embodiment, application bag 110 can be formed by a flexible tubular extrusion of plastic. After manufacture, the tube can then be cut to length. After being cut, one end is sealed or fused by known inductive welding means leaving the other end open. Other preferred embodiments can include frustroconical shapes, inverted frustroconical shapes and generally spherical shapes.

Different parts of the body can be decontaminated. In FIG. 1a, patient's appendage 150 is shown surrounded by solution applicator 100. The dimensions of the application bag vary depending on the part of the body being decontaminated. Application bag 110 should fit loosely around the body part placed inside application bag 110.

In the preferred embodiment, the general circumference of application bag 110 is at least 2 inches larger than the part of the body being decontaminated. The width of application bag 110 in a preferred embodiment is usually between 2 inches and 40 inches. In the preferred embodiment, the general length of the application bag is at least 2 inches longer than the part of the body being placed in application bag 110. The length of application bag 110 in a preferred embodiment would be between 2 inches and 60 inches. The application bag should also allow for complete articulation of any joint surrounded in order to allow for complete coverage by the antiseptic solution.

In a preferred embodiment, application bag 110 also includes fill/drain port 140. Fill/drain port 140 allows for deployment of the antiseptic solution into the application bag and draining of excess antiseptic from the application bag. Fill/drain port 140 is located generally in a position to allow for deployment of the antiseptic solution to cover the extremity. FIG. 1a is an expanded view of a preferred embodiment of fill/drain port 140. Fill/drain port 140 includes lid 180. Lid 180 seals opening in application bag 110. Lid 180 includes four parts, cap 188, threaded section 185, flexible gasket 182 and port ring 170. Cap 188 is of such minimum height that it can be easily grasped to open fill/drain port 140. Threaded section 185 width can vary in size between ¼ inch and 4 inches. Threaded section 185 is threaded to match port ring 170.

Port ring 170 is attached to opening in application bag 110 by a known adhesive or heat welding. Port ring 170 is threaded to receive threaded section 185. Port ring 170 is approximately the same depth as the threaded section 185. In the preferred embodiment the depth is between about ¼ of an inch to about 3 inches. A flexible gasket 182 is provided to seal the lid against the port ring. When lid 180 is threaded into port ring 170, bottom of lid 180 fits flush and seals against of port ring 170.

Fill/drain port 140 can be constructed from any commercially available plastic, including but not limited to polypropylene, polyethylene, or polystyrene. In other embodiments, the fill/drain port can be fitted with a quick release mechanism for removal of the antiseptic with a pump through a hose and connection fitting. Other non-threaded resealable cap and base configurations will also suffice.

Attached to open end of application bag 110 is gasket 120. Open end of application bag 110 is affixed to gasket 120 through a known adhesive or heat welding. Gasket 120 can be manufactured from synthetic rubber, such as neoprene, or a resilient plastic polymer. The gasket color can be coded to indicate the size and/or shape of the bag making for easy and error free deployment of the antiseptic solution.

Gasket 120 has a hole 130 in the in the relative center of gasket 120. Patient's appendage 150 is inserted through hole 130 and into application bag 110. In the preferred embodiment, diameter of hole 130 ranges between about 1 inch and 15 inches. However, those skilled in the art will recognize that other sizes can be provided to accommodate different patients and circumstances. Hole 130 should fit around the body extremity such as to prevent the antiseptic solution from escaping application bag 110 when in use.

Figure 2:
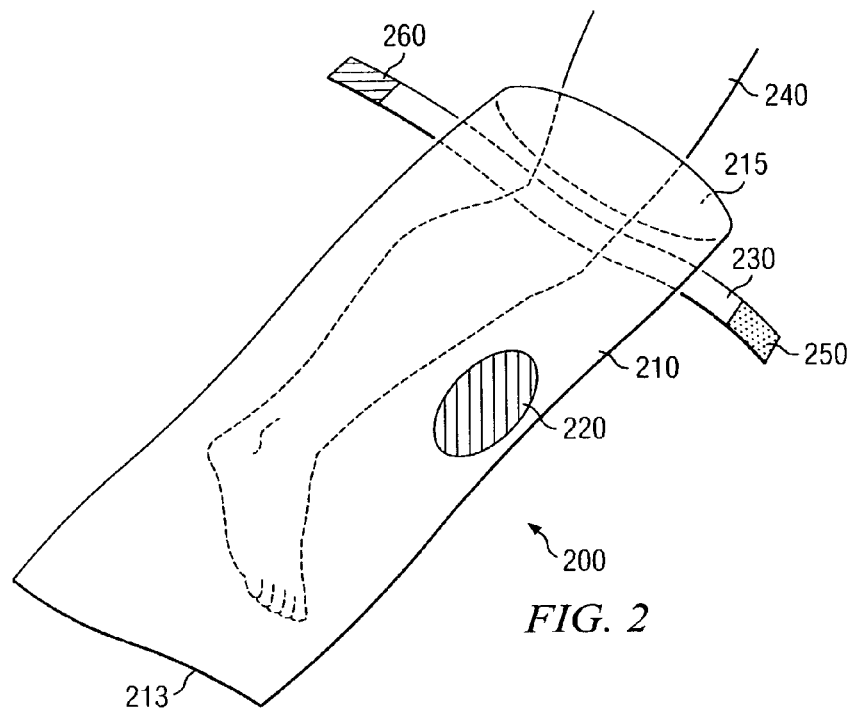
FIG. 2 is a perspective view of a preferred embodiment of the invention showing an alternate closing means.

FIG. 2 shows another preferred embodiment of solution applicator 200. Solution applicator 200 includes application bag 210 which has larger dimensions to accommodate a larger appendage such as a leg. Patient's appendage 240 is inserted into application bag 210 through opening 215 toward closed end 213. This embodiment includes solution deployment pouch 220 and a different closing means.

Application bag 210 is secured around patient's appendage 240 through the use of closing means 230. Some examples of closing means include an elastic band, adhesive tape or strap with a buckle or Velcro® closure. A preferred embodiment includes strap with a Velcro® closure. Closing means 230 allows for securing and searing application bag 210 around varying size appendages and easy adjustment. Velcro® closure includes hook section 260 and receiver section 250 as necessary to use the closing means 230 as described.

Closing means 230 is located below the opening 215 of application bag 210 but above the area to be treated with antiseptic, such that the area to be treated with antiseptic is contained within application bag 210. Closing means 230 can be attached to application bag 210 by commercially available adhesive or can be detachable.

Solution deployment pouch 220 is located on the interior of application bag 210 and contains the antiseptic to be deployed. Solution deployment pouch 220 can vary in size and shape depending on the amount of antiseptic solution contained. In the preferred embodiment, the solution deployment bag contains 2.5 liters of antiseptic solution. The solution deployment pouch may be color coded to indicate the type of antiseptic contained or may be metalized to prevent light from entering the pouch to the detriment of the antiseptic solution. In the preferred embodiment, the antiseptic to be deployed is chlorhexidine, sold under the trademark ChloraPrep® and available from Medi-Flex, Inc. of Leawood, Kans. However, other antiseptics that are effective without evaporation can also be employed.

Figure 3A:
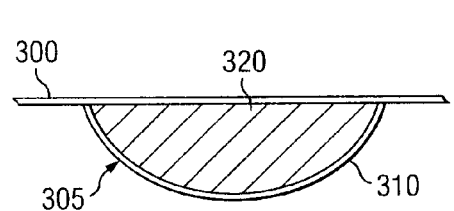
FIG. 3a is cross sectional view of a preferred embodiment of an antiseptic pouch attached to the interior of the application bag.
Figure 3B:
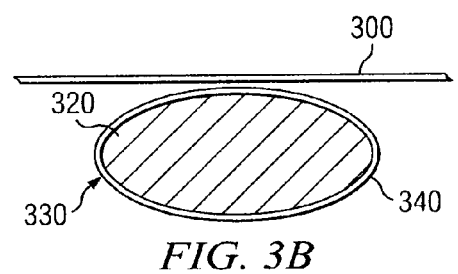
FIG. 3b is a cross sectional view of a preferred embodiment of the invention showing an antiseptic capsule attached to the interior of the application bag.

FIG. 3a and FIG. 3b illustrate two preferred embodiments for solution deployment pouch 220. As shown in FIG. 3a, a cavity 305 is created on the inside of application bag 300 by use of a cavity cover 310. The cavity cover 310 in the preferred embodiment is a hemispherical flexible container heat welded around its circumference to the interior of the application bag. The size of cavity cover 310 will depend on the amount of antiseptic solution 320 to be contained. Cavity cover 310 is of such strength that cavity cover 310 can be ruptured for use but not during normal handling and storage of the application bag. Cavity cover 310 in the preferred embodiment is formed from a 3 ml plastic sheet made of HDPE. When cavity cover 310 is ruptured, antiseptic solution 320 located in the deployment pouch is released to the interior of the application bag.

FIG. 3b shows another preferred embodiment of solution deployment pouch 220. Antiseptic solution 320 is encapsulated in capsule 330. Size and shape of capsule 330 will vary depending on the amount of antiseptic solution 320 contained. Capsule cover 340 forms the outer casing of capsule 330 and encapsulates antiseptic solution 320. Capsule 330, and the encapsulated antiseptic 320, are attached to the inside of application bag 300 by a known adhesive or spot welding. Capsule covering 340 can be manufactured from commercially available plastics. In the preferred embodiment, the covering is HDPE and is about 3 ml thick. In another embodiment the capsule can be a rigid but fractural plastic capsule contained in a cylindrical form capable of being broken for use through a set of central perforations. Capsule 330 can be attached to application bag 300 at the time of shipment to the user or could be sent separate from the application bag 300 and the user attaches capsule 330 at the time of use.

Multiple capsules or pouches can be used in a single application bag depending on the decontamination method being addressed. Further, differing antiseptic solutions can be contained in different capsules. Furthermore, sterile sponges, brushes and swabs can be contained in the capsule at the time of manufacture for use within the application bag to scrub the surgical site.

Figure 3C:
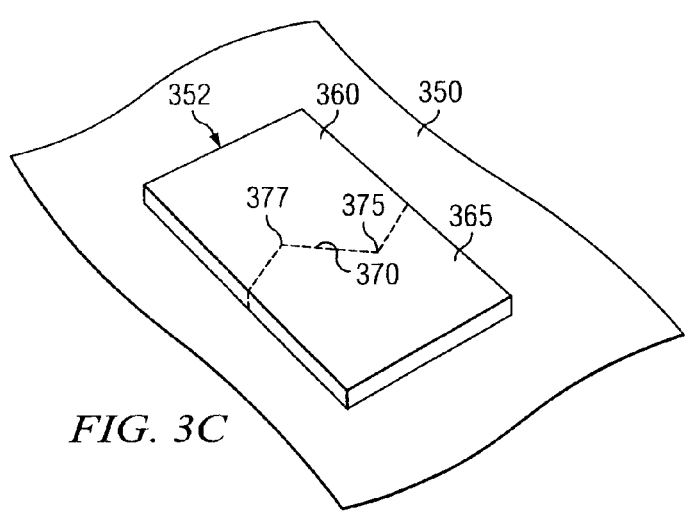
FIG. 3c is a perspective view of a puncturing device used in the preferred embodiment of the invention.

Referring now to FIG. 3c, a puncturing device is shown used in the preferred embodiment of the invention which allows for easy puncturing of the deployment pouch and/or temperature monitoring. The surface of the deployment pouch is shown as 350. Fixed to the external surface of deployment pouch 350 is a rigid plastic rectangle 352. In the preferred embodiment, the dimensions of the plastic rectangle are approximately 10 ml thick and formed of a rigid polystyrene. Other rigid plastics or light metals such as aluminum can be used as well. Plastic rectangle 352 includes halves 360 and 365 separated by a perforation 370. Perforation 370 in the preferred embodiment traverses the rectangle in an angled fashion, including two pointed extensions 375 and 377.

In use, plastic rectangle 352 is broken along perforation 370 separating the two halves 360 and 365. Pointed extensions 377 and 375 are then available to breach the surface of deployment pouch 350 thereby allowing the antiseptic fluid contained to escape into the application bag. The advantage of the use of plastic rectangle 352 is to allow controlled dispersion of the antiseptic fluid and to allow a thicker and more robust flexible plastic to be used for the deployment pouch.

In yet another embodiment, plastic rectangle 352 can include a temperature sensitive dye. The temperature sensitive dye can be used to indicate the temperature of the antiseptic contained in the deployment pouch to allow for an accurate and effective dispensing temperature or for patient comfort.

Figure 4:
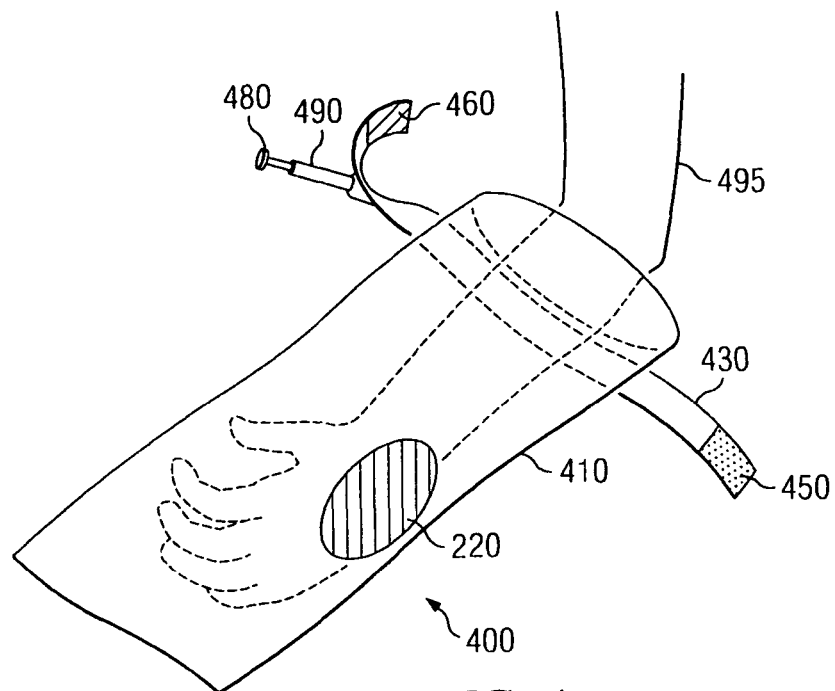
FIG. 4 is a perspective view of a preferred embodiment of the invention showing an alternate closing means.

FIG. 4 shows yet another preferred embodiment of invention. Solution applicator 400 is application bag 410 with one end sealed and one end open. Patient's appendage 495 is placed inside application bag 410 through the open end.

In this embodiment, application bag 410 is closed around patient's appendage 495 by use of pressure inflatable cuff 430. Pressure inflatable cuff 430 can be secured by any appropriate closing means 450 and 460. Specifically, a preferred embodiment for such closing means 450 and 460 is Velcro®, wherein closing means 450 is hook section and closing means 460 is receiver section. Pressure inflatable cuff 430 is located adjacent the open end of application bag 410. Pressure pump 480 inflates pressure inflatable cuff 430 through tube 490. Pressure pump 480 can be manually or mechanically inflated. Pressure inflatable cuff 430 when inflated creates a seal sufficient to prevent the antiseptic from escaping application bag 400.

Figure 5:
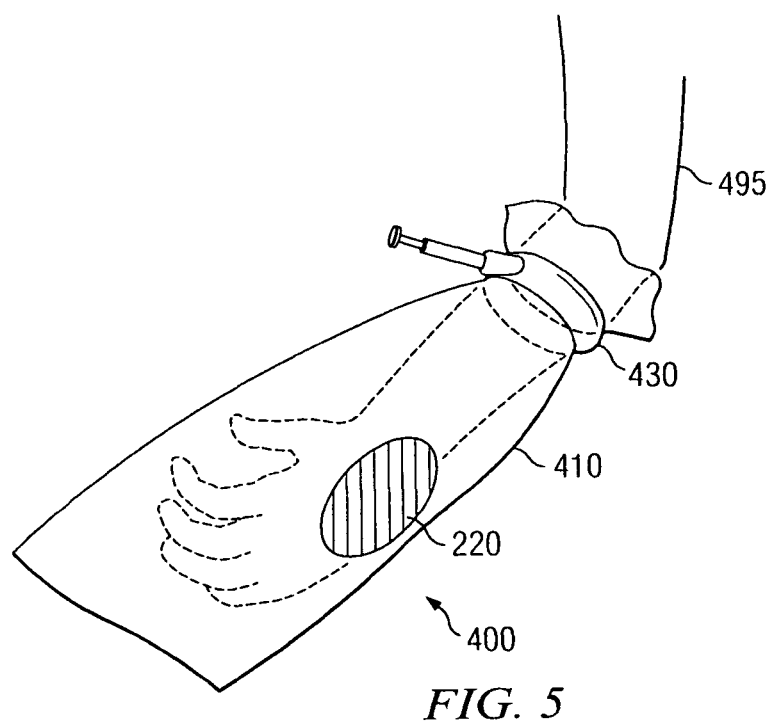
FIG. 5 is a perspective view of a preferred embodiment of the invention disclosed.

FIG. 5 illustrates solution applicator 400 when pressure inflatable cuff is inflated.

Figure 6:
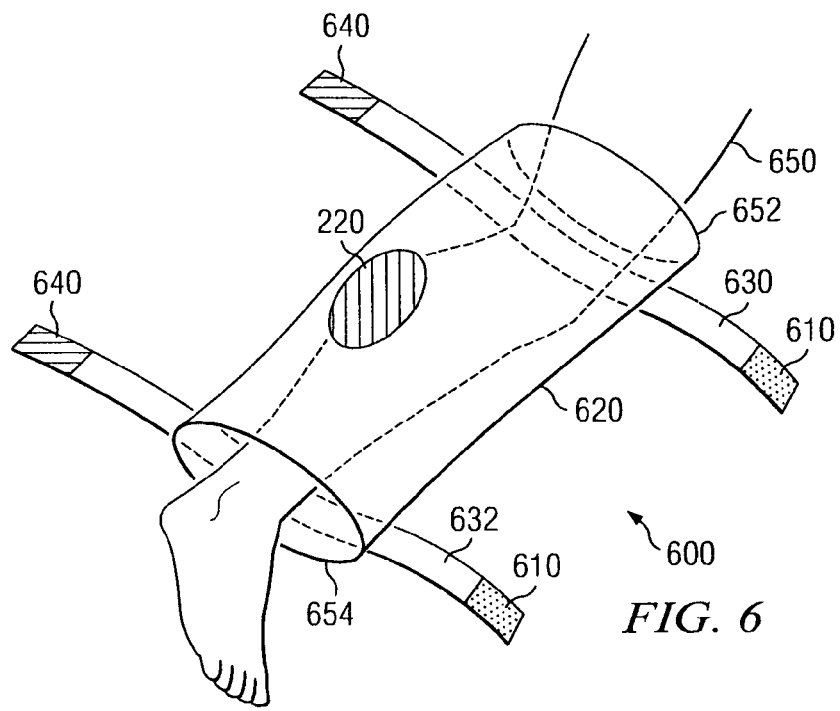
FIG. 6 is a perspective view of a preferred embodiment of the invention showing the use of two closing means.

FIG. 6 shows yet another preferred embodiment of solution applicator 600. This embodiment can be employed when only a section of a patient's appendage 650 is to be treated with antiseptic. In this embodiment, application bag 620 is open at both ends 652 and 654 and is tubular. The length of application bag 620 can vary depending on the size of the area being treated.

Each end of application bag 620 is closed around patient's appendage 650 by use of closing means 630 and 632. Each closing means is similar to those embodiments already described. For example, if Velcro® is used to secure closing means 630 and 632, Velcro® closure includes hook sections 640 and receiver sections 610 as necessary to use the closing means 630 and 632 as described. Solution deployment pouch 220 is adhered to the inside of application bag 620 between the closing means on either end.

Figure 7:
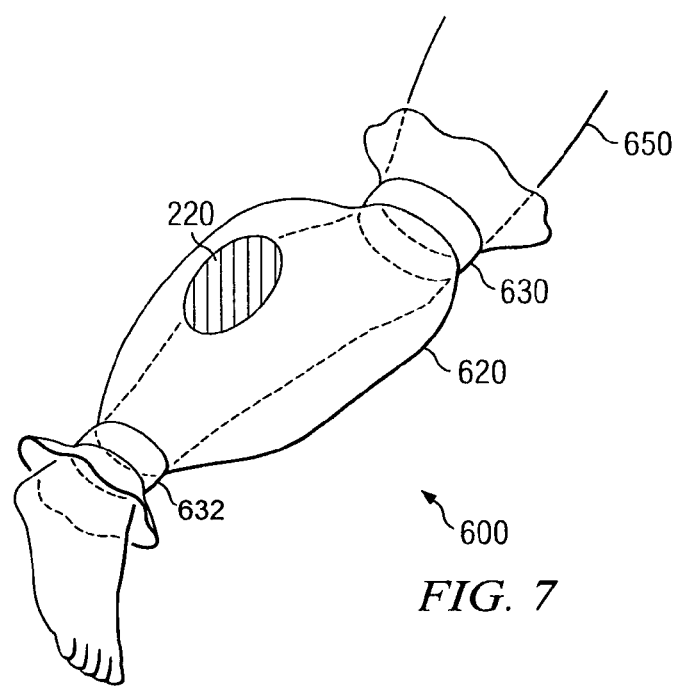
FIG. 7 is a perspective view of a preferred embodiment of the invention showing two closing means.

FIG. 7 illustrates solution applicator 600 after each end of application bag 620 has been closed around patient's appendage 650. The portion of application bag 620 between closing means is loose-fitting around patient's appendage 650. Solution deployment pouch 220 is ruptured and antiseptic fluid escapes to be massaged into the skin. All excess antiseptic is retained in the application bag 620 until closing means 630 and 632 are released and application bag 620 is removed.

Figure 8:
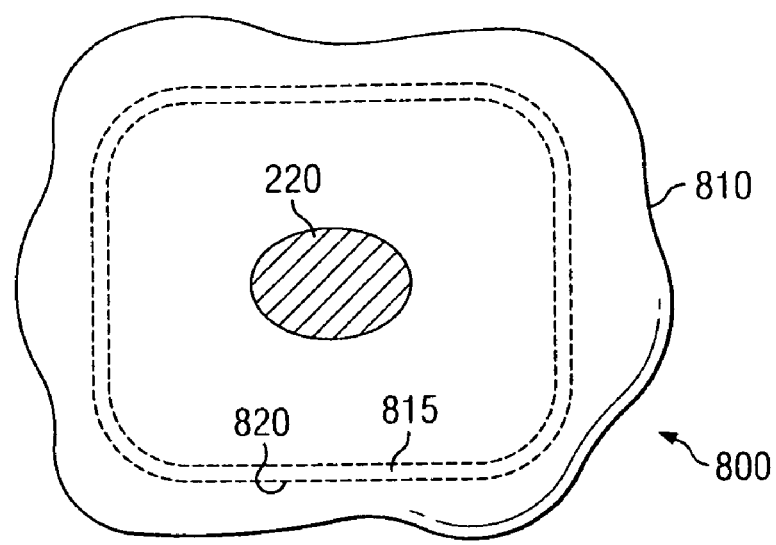
FIG. 8 is a plane view a preferred embodiment of invention.

FIG. 8 shows a preferred embodiment of solution applicator 800. Solution applicator 800 can be used to apply antiseptic to a relatively flat area of the body, such as the abdomen or back. Application bag 810 forms a generally hemispherical shape placed over the surgical site. In the preferred embodiment, application bag 810 allows a clearance of about 3 inches when attached to the patient.

The circumference of application bag 810 is lined with a disk-like adhesive strip 815. The adhesive strip is of sufficient tackiness to adhere to form a seal with the patient's skin, but still removable without injury. Suitable adhesives are well known in the art. The width of the adhesive strip should range between ¼ inch and 1 inch. In the preferred embodiment, a removable waxed tape covers the adhesive strip until such time as solution applicator will be applied to patient. Attached to the interior of application bag 810 is solution deployment pouch 220 which contains antiseptic for treatment of the patient. Deployment and use of the antiseptic fluid is similar to that described above.

Figure 9:
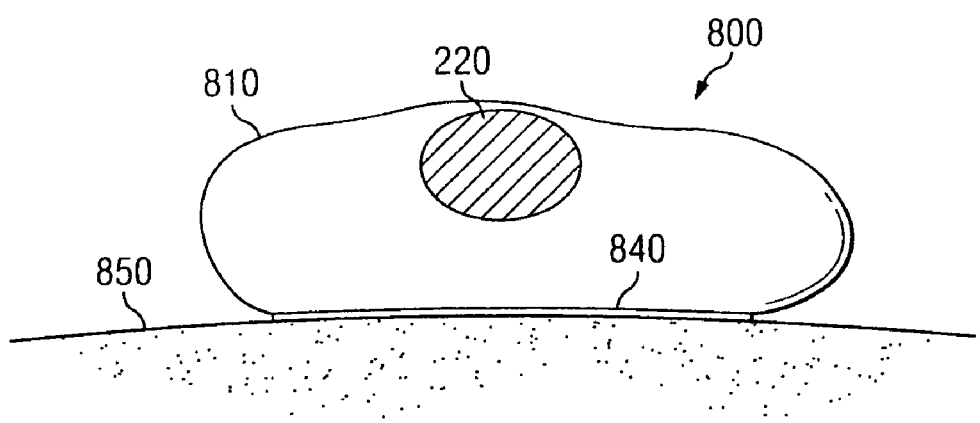
FIG. 9 is a side view of a preferred embodiment of invention.

FIG. 9 illustrates a side view of solution applicator 800 attached to abdomen of patient 850. After adhesive strip 840 is applied to the skin of the patient, the remainder of application bag 810 allows for user to maneuver application bag 810 to rub or massage the antiseptic fluid into the skin without removing adhesive strip 840 from the skin.

In use, an application bag including a deployment pouch is raised to a temperature approximately equal to that of the patient. An indication of the proper temperature is shown by the color of the plastic rectangle included on the deployment pouch. The application bag is extended and placed around the surgical site. In the preferred embodiment, the application bag is secured around the proximal end of the appendage. The distal end of the appendage resides in the interior of the application bag. Deployment pouch 220 is ruptured by breaking the plastic rectangle and breaching the deployment pouch thereby releasing the antiseptic fluid into application bag 410. The exterior of the application bag is then manipulated to assure coverage of the appendage by the antiseptic fluid. The antiseptic fluid is then rubbed or massaged into the skin through application bag 410 to dislodge biological communities. Sponges or other utensils within the bag are used to scrub the appendage if necessary. The textured internal surface of the application bag may also be used to scrub the appendage. Excess antiseptic fluid is retained by application bag 410. Since application bag 410 is transparent or substantially transparent, a visual examination of the extremity is conducted to assure that adequate and complete coverage of the surgical site has been made. Upon removal of the bag, care must be taken to insure that any portion of the non-sterile exterior of the bag does not come into contact with the now sterile extremity of the patient. To accomplish removal without contact, the neoprene gasket or adhesive strip is rolled back so that only its sterile interior is adjacent the extremity. The bag is then removed by sliding it off of the extremity, making sure that the rolled back edge is the only point of contact.

Those skilled in the art will recognize that a more complete application of antiseptic fluid can be made due to the fact that application takes place outside the operating theater. Those skilled in the art will also recognize that the antiseptic can be retained on the surgical area longer, promoting a more thorough decontamination. Those skilled in the art will also recognize that since the decontamination can take place outside the operating theater that substantial operating theater time can be saved with resulting monetary savings to the patient and the hospital.

The embodiments have been described in detail with particular reference to certain preferred embodiments thereof, but it will be understood that variations and modifications can be effected within the scope of the embodiments, especially to those skilled in the art.

The invention claimed is:

1. A containment device for deploying an antiseptic preparation to an extremity of a patient and removing bacterial colonies comprising:
   a flexible container surrounding the extremity;
   a first sealing means, attached to the flexible container, for securing a seal between the extremity and the interior of the flexible container;
   a sealable opening in the flexible container for introduction of the antiseptic preparation and wherein the antiseptic preparation is deployed and contained in the flexible container in contact with the extremity;
   a friction means for scrubbing the extremity to remove bacterial colonies included on an interior portion of the flexible container; and
   a textured surface included on an exterior portion of the flexible container for manipulation of the flexible container.

2. The containment device of claim 1 wherein the opening is a semi-rigid ring sealed by a matching and removable plug.

3. The containment device of claim 1 wherein the first sealing means comprises a flexible gasket having a circumference attached to the flexible container and a hole in contact with the extremity.

4. The containment device of claim 3 wherein the flexible gasket is comprised of a resilient plastic polymer.

5. The containment device of claim 4 wherein the gasket is color coded to indicate a size of the flexible container.

6. The containment device of claim 1 wherein the first sealing means is a removable belt.

7. The containment device of claim 1 wherein the flexible container is a plastic bag, manufactured from one of the group of high density polyethylene, low density polyethylene and ultra linear low density polyethylene.

8. The containment device of claim 1 wherein the flexible container is color coded to indicate a relationship between the patient and an operating theatre.

9. The containment device of claim 1 wherein a rupturable pouch is affixed to the interior of the flexible container and contains the antiseptic preparation.

10. The containment device of claim 9 wherein the rupturable pouch is colored to indicate a type of antiseptic preparation.

11. The containment device of claim 9 wherein the rupturable pouch is metalized.

12. The containment device of claim 9 further comprising a fracturable puncture tool fixedly attached to a surface of the rupturable pouch within the flexible container.

13. The containment device of claim 12 wherein the fracturable puncture tool further comprises a flat plastic shape bifurcated by and separable along a perforated line into at least two sections defining at least one jagged point.

14. The containment device of claim 9 wherein the fracturable puncture tool is a material demonstrating a color shift according to temperature.

15. The containment device of claim 1 further comprising a second sealing means, attached to the flexible container, for securing a seal between the extremity and the interior of the flexible container.

16. The containment device of claim 1 wherein the friction means for scrubbing the extremity to remove bacterial colonies consists of one or more of the group of raised ribs, chevron pattern, diamond pattern, and crinkling.

17. A device for applying an antiseptic to an extremity comprising:
   a collapsible tubular membrane having an open end, an exterior surface, and an interior surface;
   a flexible seal at the open end of the collapsible tubular membrane;
   an antiseptic insertion means in the collapsible tubular membrane for introduction of the antiseptic into the collapsible tubular membrane adjacent the extremity;
   a frictional scrubbing means, formed on the interior surface, for manually removing contaminants from the extremity; and,
   a textured surface, formed on the exterior surface for manipulation of the collapsible tubular membrane.

18. The device of claim 17 wherein the frictional scrubbing means is a textured surface having a pattern consisting of one or more of the group of raised ribs, chevrons, diamonds, and crinkling.

19. The device of claim 17 wherein the frictional scrubbing means is a sponge within the collapsible tubular membrane.

20. The device of claim 17 wherein the antiseptic insertion means includes an opening and a cap securable within the opening forming a resealable port.

21. The device of claim 17 wherein the antiseptic insertion means is a breakable bubble on the interior of the collapsible tubular membrane which contains the antiseptic to be applied.

22. The device of claim 17 wherein said antiseptic insertion means is a breakable capsule which contains the antiseptic to be applied and wherein the capsule is adhered to the interior of the tubular membrane.

23. The device of claim 17 wherein the flexible seal is a resilient plastic polymer disk.

24. The device of claim 17 wherein the flexible seal is an elastic band.

25. The device of claim 17 further comprising an antiseptic temperature indicator in heat conductive contact with the antiseptic to be applied.

26. The device of claim 17 wherein said antiseptic insertion means includes one or more of the group of a resealable port, a bubble, a capsule, and any combination thereof.

* * * * *